(12) United States Patent
Prescott

(10) Patent No.: US 7,891,485 B2
(45) Date of Patent: Feb. 22, 2011

(54) SUTURE RETAINER WITH RIB MEMBERS

(75) Inventor: Michael Prescott, Hamden, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/409,127

(22) Filed: Mar. 23, 2009

(65) Prior Publication Data

US 2009/0255836 A1   Oct. 15, 2009

Related U.S. Application Data

(60) Provisional application No. 61/044,149, filed on Apr. 11, 2008.

(51) Int. Cl.
A61B 17/06 (2006.01)
(52) U.S. Cl. .................. 206/63.3; 206/227; 206/380
(58) Field of Classification Search ............ 206/63.3, 206/227, 339, 363, 370, 380, 438
See application file for complete search history.

(56) References Cited

U.S. PATENT DOCUMENTS

| | | | |
|---|---|---|---|
| 4,961,498 A * | 10/1990 | Kalinski et al. ............ 206/339 |
| 4,967,902 A | 11/1990 | Sobel et al. | |
| 5,052,551 A | 10/1991 | Cerwin et al. | |
| 5,154,283 A | 10/1992 | Brown | |
| 5,165,217 A | 11/1992 | Sobel et al. | |
| 5,180,053 A | 1/1993 | Cascio et al. | |
| 5,213,210 A * | 5/1993 | Cascio et al. ............ 206/380 |
| 5,230,424 A * | 7/1993 | Alpern et al. ............ 206/63.3 |
| 5,261,210 A | 11/1993 | Brown | |
| 5,284,240 A | 2/1994 | Alpern et al. | |
| 5,341,922 A * | 8/1994 | Cerwin et al. ............ 206/63.3 |
| 5,350,060 A | 9/1994 | Alpern et al. | |
| 5,359,831 A | 11/1994 | Brown et al. | |
| 5,417,036 A | 5/1995 | Brown | |
| 5,462,162 A | 10/1995 | Kaplan et al. | |
| 5,468,252 A | 11/1995 | Kaplan et al. | |
| 5,628,395 A * | 5/1997 | Daniele et al. ............ 206/63.3 |
| 5,655,652 A * | 8/1997 | Sobel et al. ............ 206/63.3 |
| 5,833,055 A * | 11/1998 | Cerwin et al. ............ 206/63.3 |
| 5,906,273 A | 5/1999 | Pohle et al. | |
| 6,047,815 A * | 4/2000 | Cerwin et al. ............ 206/63.3 |
| 6,105,339 A | 8/2000 | Pohle et al. | |
| 6,135,385 A | 10/2000 | Martinez de Lahidalga | |
| 6,464,071 B2 | 10/2002 | Baumgartner | |

(Continued)

FOREIGN PATENT DOCUMENTS

EP        0749725        12/1996

(Continued)

OTHER PUBLICATIONS

European Search Report for EP 09251064.3-2310 date of completion is Aug. 18, 2009 (4 pages).

*Primary Examiner*—Bryon P Gehman

(57) ABSTRACT

The present disclosure describes a suture retainer including a one-piece retaining structure having a passageway formed therein for receiving at least one suture, wherein the passageway includes a substantially open top portion, a substantially closed bottom portion, at least one radial turn and a plurality of rib members positioned along the radial turn of the passageway, wherein the rib members and the passageway are unitarily formed in a fixed position.

15 Claims, 3 Drawing Sheets

U.S. PATENT DOCUMENTS 6,481,568 B1 * 11/2002 Cerwin et al. .............. 206/63.3
6,533,112 B2    3/2003 Warnecke

FOREIGN PATENT DOCUMENTS

| | | |
|---|---|---|
| EP | 0797954 | 10/1997 |
| EP | 0931511 | 7/1999 |
| EP | 1498076 | 1/2005 |
| WO | WO 0058156 | 10/2000 |

* cited by examiner

SUTURE RETAINER WITH RIB MEMBERS

CROSS-REFERENCE TO RELATED APPLICATION

The present application claims the benefit of and priority to U.S. Provisional Application Ser. No. 61/044,149, filed on Apr. 11, 2008, the entire disclosure of which is incorporated herein by reference.

BACKGROUND

1. Technical Field

The present disclosure relates to suture retainers, and more particularly to suture-retainers made from one-piece retaining structures.

2. Discussion of Related Art

There are many suture packages known in the art, including suture retainers as described in U.S. Pat. Nos. 5,052,511; 5,154,283; 5,246104; 5,261,210; 5,359,831; 5,417,036; 5,462,162; 5,906,273; 6,076,659; and 6,135,272. These retainers may be defined as having either: an oval-shaped area to retain one or more sutures in an overlapping coiled configuration; or a continuous oval retaining area to maintain one or more sutures in a spiraling non-overlapping oval configuration. In either instance, the retainers are known to be formed from two mating components, such as a base and a cover, to secure the suture in the suture retaining area. However, only in the instance of an overlapping coiled configuration are retainers known to be formed from a one-piece retaining structure.

An important aspect of the design and manufacture of suture packages is that the suture should be removable from the retainer without becoming entangled with itself, entangled with the retainer, kinked, coiled or bound in undesirable ways. In the case of the retainers using the overlapping coil configuration, whether made from a one-piece retaining structure or two mating components, the suture may become entangled with itself prior to use or may be pulled taught against itself while being removed from the package. In the case of the retainers using the spiraling non-overlapping oval configuration, the suture may become entangled in a gap in the interface between the base and the cover prior to use (also known as the "capstan effect") or may be pulled taught against the retaining area while being removed from the package. Such problems cause the removal of the suture from the retainer to become more difficult, time-consuming, and in extreme cases, damaging to the suture.

This problem may also occur in one-piece structures which include movable or pivotable parts, such as those packages described in U.S. Pat. Nos. 4,967,902 and 5,165,217. These packages include a multiplicity of door means hingingly attached to channels designed for storing the suture. The door means is described as having to pivot from an open position to a closed position over the suture channel to maintain the suture in the channel. Similar to the two-piece structure, these one-piece suture packages are still capable of snagging the suture at the position where the door means meets the channel wall. As described in both disclosures referenced above, the packages further require fins and standoffs to prevent the suture from binding or becoming entrapped in the door locking means.

As a result, recent emphasis has been placed on creating packaging for sutures which decreases or eliminates the possibility of a portion of the suture binding to gaps in the suture package or other portions of the suture.

SUMMARY

Accordingly, the present disclosure provides novel retainers for surgical sutures which eliminate many problems associated with the prior art suture retainers.

A suture retainer is disclosed which includes a one-piece retaining structure having a passageway formed therein for receiving at least one suture. The passageway includes a substantially open top portion, a substantially closed bottom portion, at least one radial turn and a plurality of rib members positioned along the radial turn of the passageway for preventing the sutures from becoming bound to one another. The passageway and the rib members being unitarily formed in a fixed position to form a continuous path for the suture and eliminate the possibility of the suture being bound in a gap created by a two-piece retainer or a one-piece structure with moving parts.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION THE DRAWINGS

Figure 1:
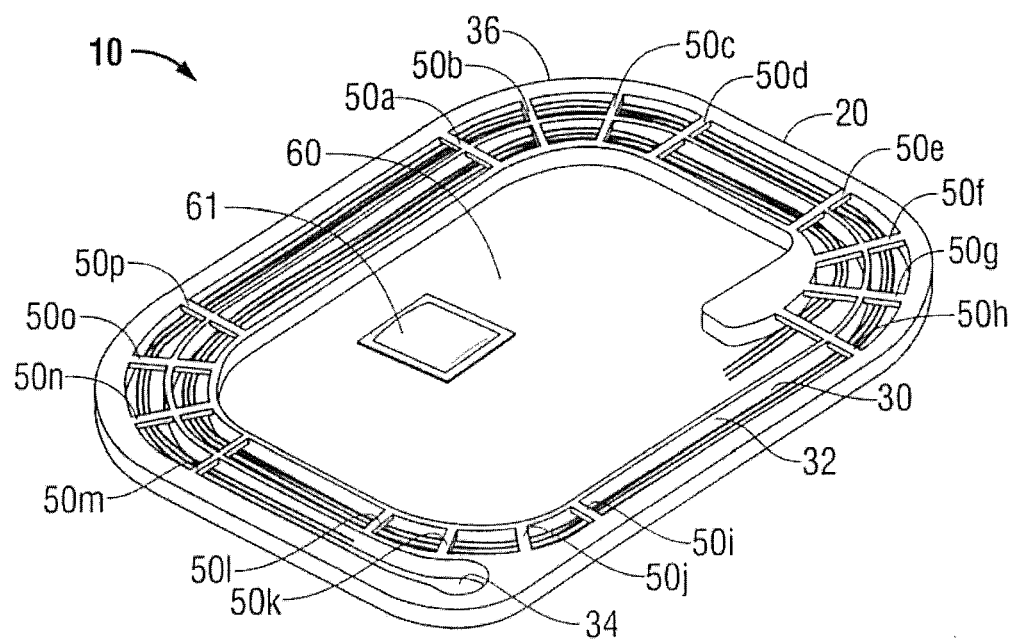
FIG. 1 is a perspective view of a one-piece suture retainer.

Embodiments of the presently disclosed suture package will now be described in detail with reference to the figures, in which like reference numerals identify corresponding elements throughout the several views.

Unless otherwise specified, any further reference to sutures should be understood to refer to any suture, including but not limited to monofilament sutures, multifilament sutures, coated sutures, barbed sutures, hollow sutures, armed sutures, unarmed sutures, double-armed sutures, and the like. FIG. 1 illustrates a first embodiment of a suture retainer 10 as will be discussed herein. Suture retainer 10 includes retaining structure 20 having passageway 30 formed therein. Passageway 30 is configured to receive at least one suture 40 and includes open top portion 32, closed bottom portion 34, at least one radial turn 36 and a plurality of rib members 50*a-p*. Rib members 50*a-d* are shown positioned intermittently along portions of radial turn 36 to retain sutures 40 in passageway 30. Rib members 50*a-d* and passageway 30 are unitarily formed in a fixed position. Retaining structure 20 is further shown including recess 60 which in some embodiments includes stabilizing element 61.

The retaining structure may be manufactured using any suitable moldable material known to those skilled in the art. In embodiments, the structures may be formed using moldable plastics, such as polypropylene, polyethylene, polysulfone, polyethylene terethphalate, and other suitable polymeric materials. The presently described retaining structures are often injection molded, however, the structures may be formed by any other conventional processes and equivalents thereof including thermoforming processes.

Figure 2A:
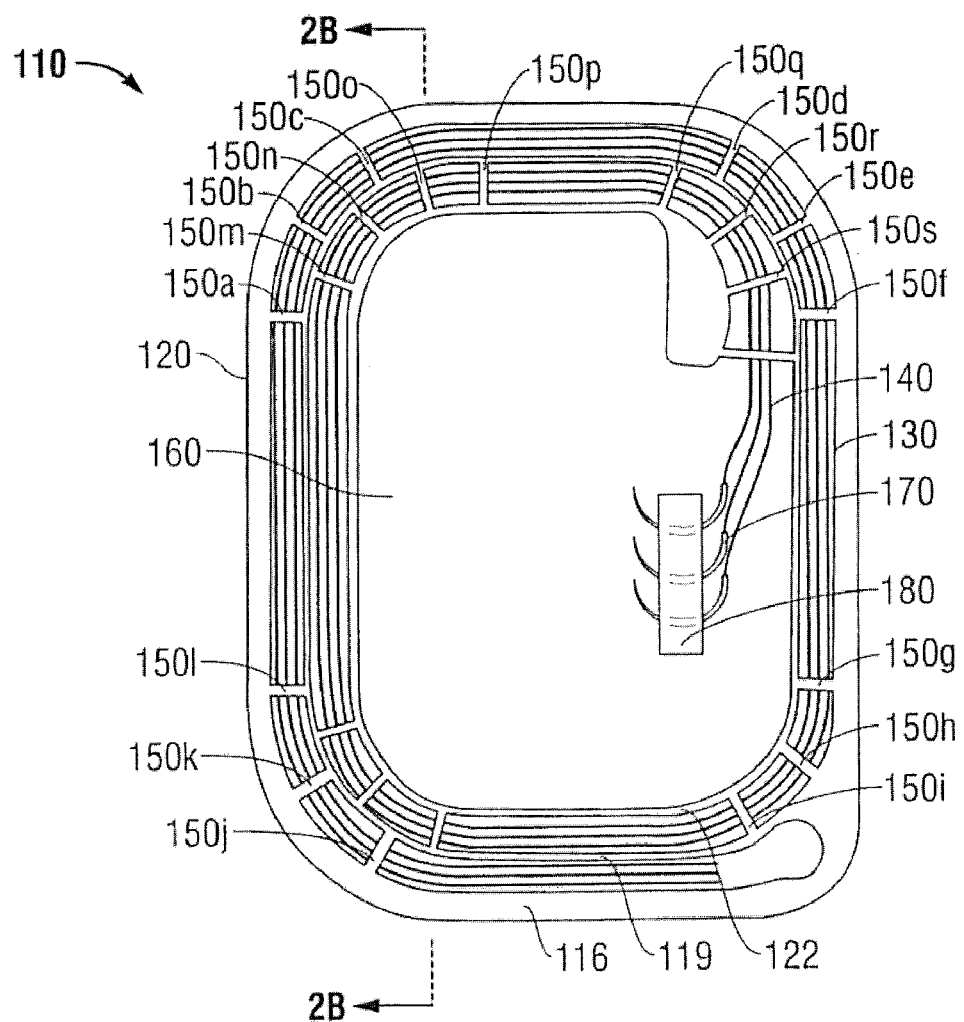
FIG. 2A is top view of a one-piece suture retainer.
Figure 2B:
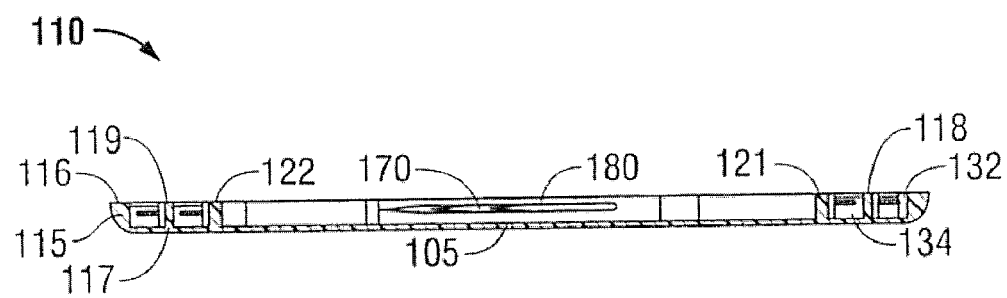
FIG. 2B is a side cross-sectional view of the suture retainer illustrated in FIG. 2A and shown along line B1-B2.

Referring now to FIGS. 2A and 2B, there is shown a top view and a side cross-sectional view, respectively, of an embodiment of a suture retainer 110 for maintaining and dispensing sutures in accordance with the present disclosure. Suture retainer 110 includes retaining structure 120 which contains base 105 which includes outer wall 115 and inner wall 117. Outer wall 115 rises from base 105 and extends around the outer circumference of base 105. Outer wall includes outer rim 116. Inner wall 117 also rises from base 105, but extends around an inner portion of retaining structure 120 in a generally oval pattern spiraling toward the center of structure 120. Inner wall 117 includes a first inner portion 118 which begins to spiral toward the center of structure 120 while generally following the shape of outer wall 115, and a second inner portion 121 which continues to spiral toward the center of structure 120 while generally following the shape of first inner portion 118 of inner wall 117. Although FIGS. 2A and 2B include a first and second inner portion, it is envisioned that the suture retainers described herein may include any number of inner portions, i.e., third inner portions, fourth inner portions, fifth inner portions, etc., as required to create any number of loops in the passageway as the inner wall continues to spiral towards the center of the retainer. First inner portion 118 of inner wall 117 includes a first inner rim 119 and second portion 121 of inner wall 117 includes second inner rim 122. Rib members 150a-s are shown connecting intermittent portions of outer rim 116 to first inner rim 119 and also connecting intermittent portions of first inner rim 119 to second inner rim 122. Recess 160 includes needle park assembly 180 which is shown storing needles 170 attached to sutures 140.

Passageway 130 is defined within one-piece retaining structure 120 by outer wall 115, inner wall 117 and base 105. In embodiments, outer wall 115 and inner wall 117 rise from base 105 resulting in passageway 130 having a closed bottom portion 134. In embodiments, open top portion 132 of passageway 130 is positioned between each of rib members 150a-s which are positioned intermittently along passageway 130 to connect small portions of outer rim 116, first inner rim 119 and second inner rim 122.

The rib members are designed to maintain the sutures in the passageway defined within the retaining structure. In addition, the rib members are part of the one-piece retaining structure and as a result prevent the sutures from becoming entangled with the retaining structure during withdrawal of the suture prior to use. In embodiments, the rib members may connect the outer rim to the first inner rim, the first inner rim to the second inner rim, and so on, through a common point of intersection positioned along the first inner rim, as shown in FIG. 1. In embodiments, the rib members may connect the outer rim to the first inner rim, the first inner rim to the second inner rim, and so on, in a staggered configuration wherein a common point of intersection along first inner rim does not exist, as shown in FIG. 2. It is envisioned that the number of rib members needed to maintain the suture in the passageway may vary depending upon the size of the retaining structure, the number of radial turns, the size of the suture, the suture material, the quantity of the sutures, and the material used to form the retaining structure.

Retaining structure 120 further includes recess 160 which is positioned near the center of the structure. Recess 160 is defined within retaining structure 120 by base 105 and inner wall 117 thereby being accessible from the top. It is envisioned that the size of recess 160 may vary according to the configuration of passageway 130, but in embodiments, recess 160 will be of sufficient size to receive at least one of the following items: a suture, a needle park assembly, needles, a stabilizing element, pledget materials and combinations thereof.

A needle park assembly 180 may be positioned within recess 160 of retaining structure 120. Any needle park assembly known to one having ordinary skill in the art may be used to receive a needle. See, for example, U.S. Pat. Nos. 6,481,569, 5,788,062, 5,472,081, 5,180,053, 5,131,533, 5,099,994, and 4,424,898. Needle park assembly is designed to accommodate a surgical needle of any known size and shape. Retaining structure 120 is a one-piece structure which does not require a cover and as a result allows easy access into recess 160 for suture-removal from structure 120. Surgical personnel can gain access to the armed suture through uncovered recess 160 and remove armed suture 140 by disengaging needle 170 from needle park assembly 180 and then pulling suture 140 from passageway 130.

In embodiments, the needle park assembly may be positioned outside the recess. The needle park may be positioned anywhere on the retaining structure. In embodiments, the needle park may be positioned on top of the retainer. In embodiments, the needle park may be positioned on the bottom of the retaining structure. In still other embodiments, more than one needle park assembly may be positioned on either end of the suture passageway and/or on the top and bottom of the retaining structure and any combination thereof.

Recess 160 may further include a stabilizing element (see FIG. 1) Stabilizing elements are added to the suture retainer to maintain the moisture content inside the retainer at acceptable limits. Package stabilizing elements are known in the art and include a carrier, often made from paper or other cellulosic material, which may or may not be impregnated with or contain a stabilizing agent. The stabilizing agent is meant to absorb moisture in the retainer and may be any suitable material capable of controlling moisture in the retainer. The stabilizing agent should be free of any appreciable toxicities which may be harmful to the body upon implantation of the suture stored in the retainer. Some non-limiting examples are described in U.S. Pat. No. 5,246,104, the entire content of which is incorporated herein by reference.

In embodiments, recess 160 may further include a label element (not shown). The label element is intended to include printed matter such as graphics and/or text which may be useful in identifying the products stored in the retainer. In embodiments, the labeling element may further be made from a material which is useful as a stabilizing agent.

Figure 3:
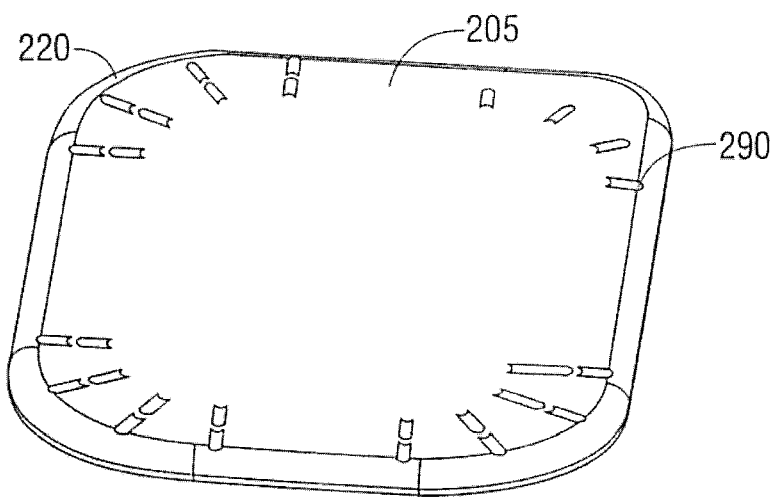
FIG. 3 is a perspective view of an embodiment of a suture retainer.

Turning now to FIG. 3, an embodiment is disclosed wherein the base 205 of retaining structure 220 is shown including at least one vacuum aperture 290. In embodiments, vacuum apertures 290 are aligned with portions of the passageway defined within the retaining structure and may be used to load the sutures into the passageway. As is known in the art, loading may be accomplished by applying a vacuum to one of or a series of the vacuum aperture to draw the suture into the passageway of the retaining structure. The vacuum may be applied to a variety of different vacuum apertures to move the suture along in the passageway. Any suitable method for vacuum loading the suture into the retaining structure is envisioned.

Figure 4:
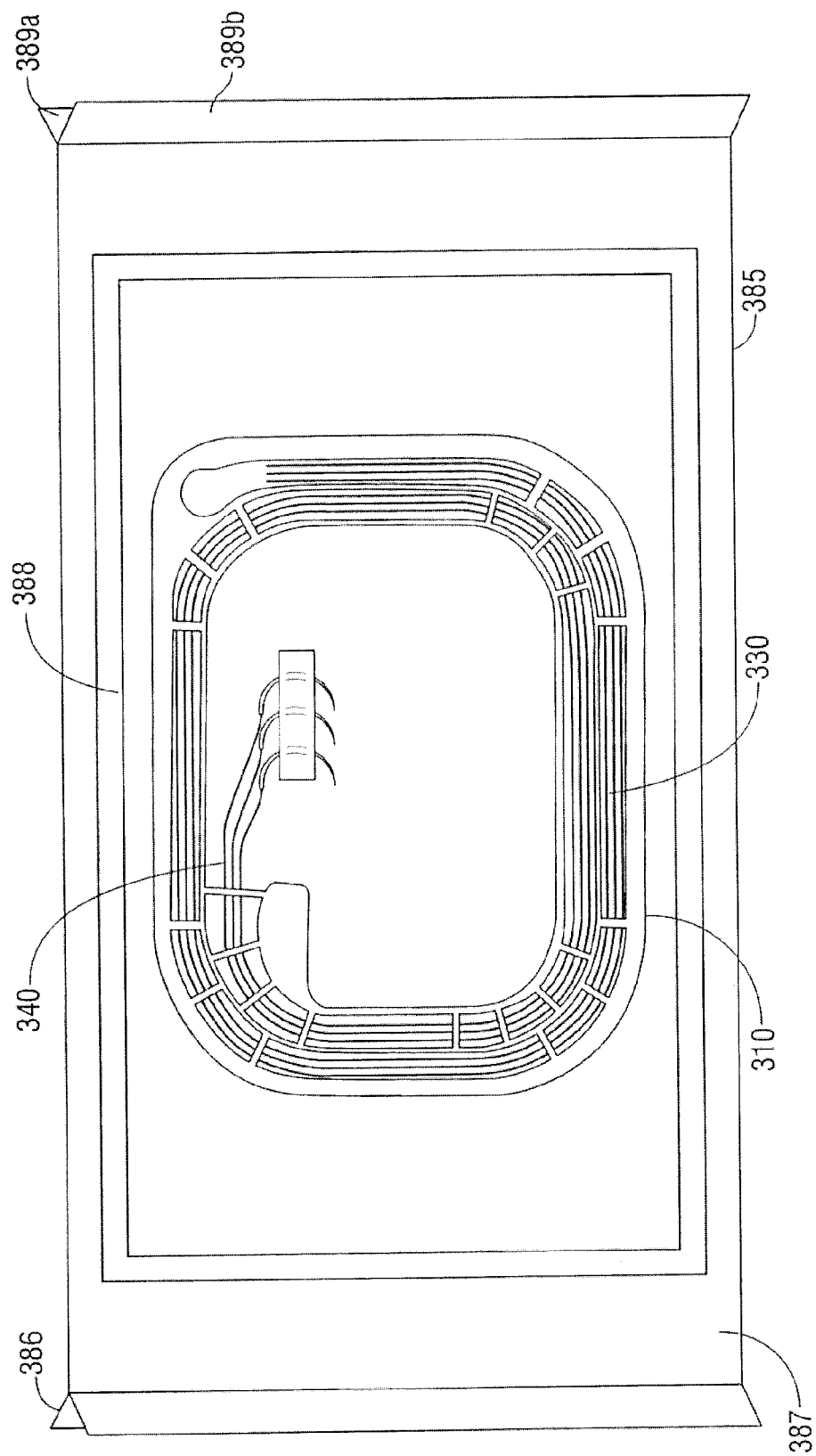
FIG. 4 is top view of a one-piece suture retainer described herein.

Referring now to FIG. 4, suture retainer 310 is shown enclosed in a second container 385. In embodiments, retainer 310 does not include a cover sheet to store sutures 340 in passageway 330, but is enclosed in a second breathable container to maintain sterility of retainer 310 and its contents. In the case of nonabsorbable sutures, the suture 340 and the retainer 310 may be simply enclosed in breathable second container 385 which is suitable for sterilization. Breathable second container 385 includes a back panel 386 which may be made from a polyolefin (Tyvek) or paper or other material compatible with known sterilization methods and a front panel 387 which is formed from a clear plastic, such as polyethylene. The two panels are attached to one another via adhesive 388 positioned along the perimeter. Breathable container 385 can be opened by pulling apart tabs 389a-b to open the container and retrieve suture retainer 310.

In the case of absorbable sutures, the retainer would need to be sealed in a second container which is not only sealed for sterility purposes but also sealed to prevent moisture from entering the retainer. Absorbable sutures are subject to hydrolytic degradation, and therefore must be packaged in an airtight sealed container which is substantially impervious to water. Typical air-tight packaging includes a laminate film having a metallic foil layer. One known method of "bone dry" packaging of absorbable sutures is described in U.S. Pat. No. 3,728,839 to Glick, the entire contents of which are incorporated herein by reference. In this method, the gaseous contents of the suture retainer are either evacuated or replaced with a gas which is inert towards the absorbable suture prior to sealing the packaging. In some embodiments, the retaining structure may be positioned with a second container such as a foil envelope, which may then be received within a third container, such as a breathable container described herein. In some embodiments, the retainer may simply include a cover sheet which is configured and designed to overlie the top of the retainer.

In embodiments, the molded retainer may include a removable cover sheet which is configured and dimensioned to overlie the top of the suture retainer. In embodiments, the cover sheet is adhesively attached to portions of the outer rim of the retaining structure and may cover any or all of the passageway, the recess, and all the contents received in the retainer. It is envisioned that the cover sheet may be peeled away from the retaining structure to allow access to the sutures positioned within the retainer. Although not necessary to maintain the sutures in the retaining structure, the cover sheet may be useful in sealing the retaining structure from moisture and contamination. In some embodiments, the cover sheet may be mechanically attached to the retaining structure. For example, the cover sheet may be made of a moldable plastic which is configured and dimensioned to snap onto the retaining structure. The cover sheet is often made of a foil, paper or polymeric material and in some embodiments may include a portion that is transparent as to allow a user to see the contents received in the retainer without removing the cover sheet. It is envisioned that the cover sheet may be made from a material suitable for acting as a stabilizing agent and/or may include printed matter, such as graphics and/or text to assist in identifying the contents of the retainer.

In additional embodiments, it is contemplated that the suture retainer may further include an injection port for allowing the passage of an agent between the outside of the retainer and the sutures positioned in the passageway defined in the retainer. The injection port may be positioned on the retainer itself or may be positioned on the cover sheet which overlays the retainer. Such a port would allow the passage of any suitable agent, including but not limited to, drugs, viable cells, growth factors, diluents, proteins, and any other bioactive or non-bioactive agents.

It will be understood that various modifications may be made to the embodiments disclosed herein. For example, although the above embodiments are described with reference to a surgical suture retainer, it is contemplated that the disclosure is not limited to such an application and may be applied to various medical instruments. Additionally, although the illustrative embodiments described herein disclose a single passageway defined within the retaining structure, it is contemplated that multiple passageways may be defined within the retaining structure. In another example, rather than defining the passageway in a generally spiral configuration, the passageway may be defined in any configuration which includes at least one radial turn, such as a zig-zag formation. Therefore, the above description should not be construed as limiting, but merely as exemplifications of preferred embodiments. Those skilled in the art will envision other modifications within the scope and spirit of the claims.

What is claimed is:

1. A suture retainer comprising:
a one-piece retaining structure having a passageway formed therein for receiving at least one suture, wherein the passageway includes an open top portion, a closed bottom portion, at least one radial turn and a plurality of rib members positioned along the at least one radial turn of the passageway, the rib members and the passageway being unitarily formed in a fixed position, the rib members directly connecting intermittent portions of an outer rim of the outer wall to an inner rim of the inner wall across the at least one radial turn of the passageway; wherein the open top portion of the passageway is positioned between each of the rib members, and the rib members are not movable.

2. The suture retainer of claim 1 wherein the passageway is substantially spiral.

3. The suture retainer of claim 1 further comprising a recess.

4. The suture retainer of claim 3 further comprising a needle park assembly positioned in the recess.

5. The suture retainer of claim 3 further comprising a stabilizing element positioned within the recess.

6. The suture retainer of claim 1 further comprising at least one vacuum aperture positioned along a bottom portion of the passageway for loading the sutures into the retainer.

7. The suture retainer of claim 1 wherein the retainer is made from a material selected from the group consisting of polypropylene, polyethylene, polysulfone, polyethylene terethphalate, and combinations thereof.

8. The suture retainer of claim 1 wherein the retainer is injection molded.

9. The suture retainer of claim 1 wherein the retainer is thermoformed.

10. The suture retainer of claim 1 further comprising a second container for receiving the one-piece retaining structure.

11. The suture retainer of claim 10 wherein the second container is a breathable container.

12. The suture retainer of claim 10 wherein the second container is a foil pouch.

13. The suture retainer of claim 1 further comprising a cover sheet.

14. The suture retainer of claim 13 further comprising a needle park assembly positioned on the cover sheet.

15. A suture retainer comprising:
a one-piece retaining structure having a passageway for receiving at least one suture, and defined therein by a base, an outer wall rising from the base, and an inner wall rising from the base, wherein the passageway includes at least one radial turn and a plurality of rib members, the rib members and the passageway being unitarily formed in a fixed position, the rib members directly connecting intermittent portions of an outer rim of the outer wall to an inner rim of the inner wall across the at least one radial turn of the passageway, and the rib members are not movable.

* * * * *